United States Patent [19]
Fischell

[11] Patent Number: 4,731,083
[45] Date of Patent: Mar. 15, 1988

[54] MANUALLY ACTUATED HYDRAULIC SPHINCTER

[75] Inventor: Robert E. Fischell, Silver Spring, Md.

[73] Assignee: The Johns Hopkins University, Baltimore, Md.

[21] Appl. No.: 770,448

[22] Filed: Aug. 29, 1985

Related U.S. Application Data

[62] Division of Ser. No. 421,441, Sep. 21, 1982, Pat. No. 4,571,749.

[51] Int. Cl.⁴ ............................................. A61F 2/02
[52] U.S. Cl. .............................. 623/14; 128/DIG. 25
[58] Field of Search ........................ 128/1 R; 623/11; 128/DIG. 25

[56] References Cited
U.S. PATENT DOCUMENTS 4,433,440 2/1984 Cohen ..................................... 623/8

Primary Examiner—Richard J. Apley
Assistant Examiner—David J. Isabella
Attorney, Agent, or Firm—Robert E. Archibald; Howard W. Califano

[57] ABSTRACT

An implantable hydraulic urinary sphincter system is disclosed for maintaining continence in those patients unable to control or stop inadvertent urrinary flow. The invented apparatus generally consists of an artificial urinary sphincter and a control means for obtaining continence while causing the artificial sphincter to apply mininmal pressure to the urethra for all conditions of the bladder. The invented apparatus: (1) automatically causes sphincter fluid pressure to increase or decrease with sensed bladder and/or abdominal pressure, and (2) is manually actuated by the patient when he or she desires to urinate. The invented apparatus can be filled with fluid, or the fluid pressure can be reset, after implantation without necessitating a surgical procedure.

12 Claims, 13 Drawing Figures

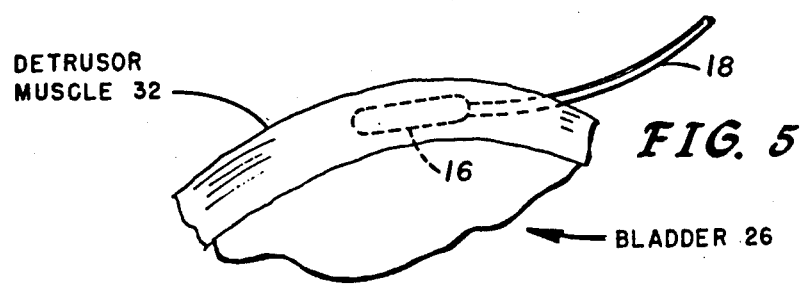
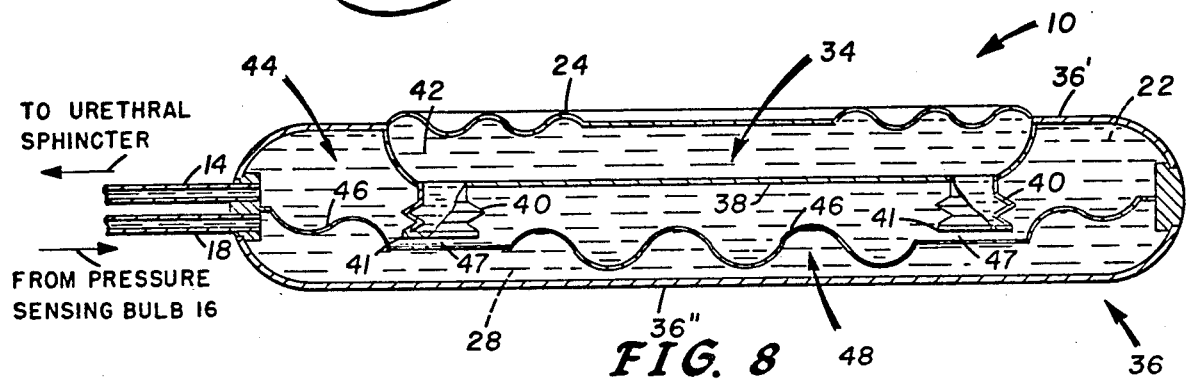
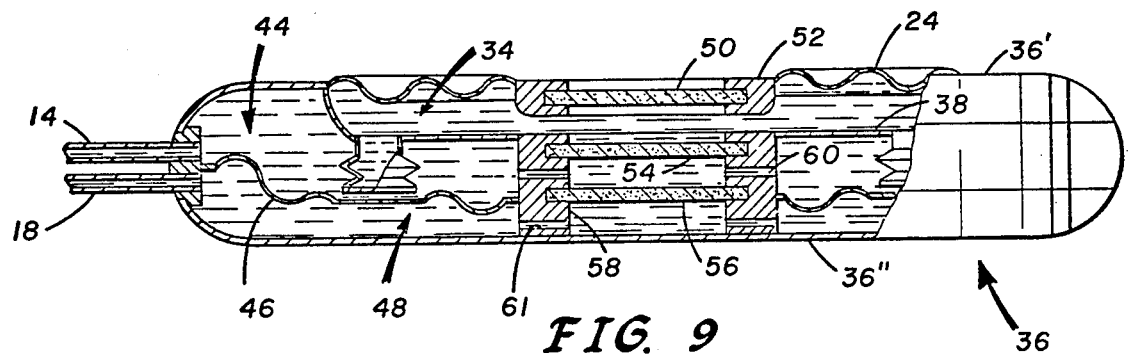
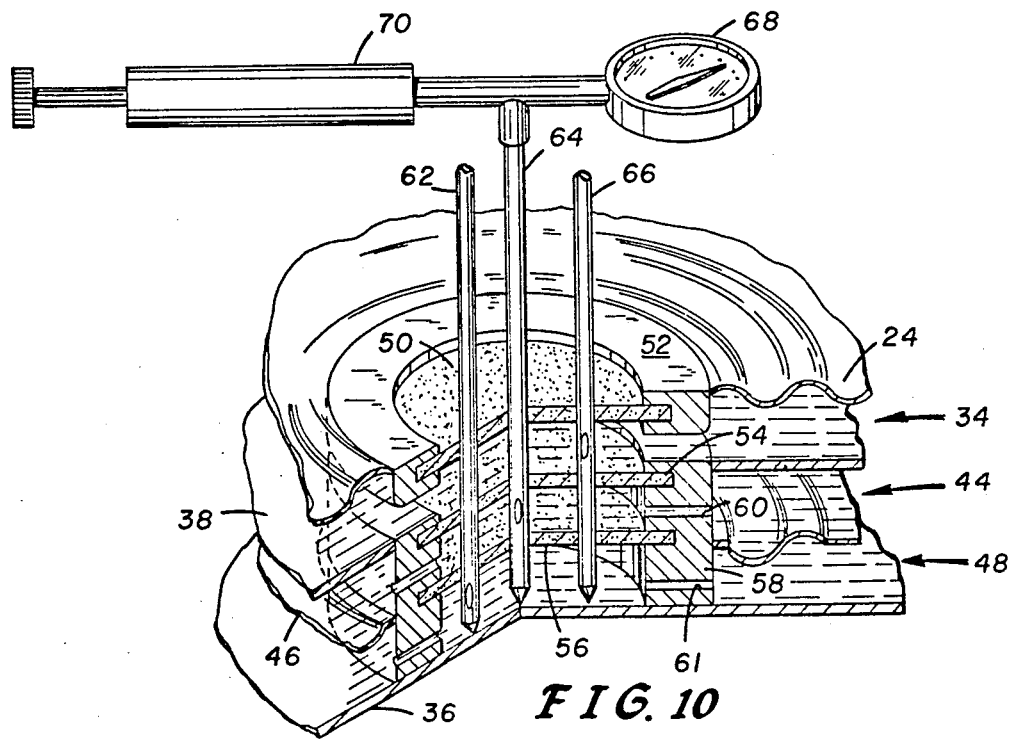

MANUALLY ACTUATED HYDRAULIC SPHINCTER

This is a divisional of co-pending application Ser. No. 421,441, filed on Sept. 21, 1982, now U.S. Pat. No. 4,571,749.

BACKGROUND OF THE INVENTION

1. Field of the Invention

The invention relates to an artificial sphincter for maintaining continence in those patients unable to control or stop inadvertent urinary flow. More particularly, the invention relates to a hydraulic sphincter (MAHS) which: automatically causes sphincter pressure to increase or decrease with bladder pressure and/or abdominal pressure; is manually actuated by the patient when he or she desires to urinate; and, allows sphincter fluid pressure to be measured and adjusted after implantation without necessitating a surgical procedure.

2. Description of the Prior Art

Urinary incontinence is a ubiquitous disorder which represents more than a personal inconvenience and social problem. For many, particularly those individuals suffering spinal injury, incontinence can cause life threatening complications. In the United States alone, it is estimated that 100,000 persons of all ages, many of them young veterans, have sustained spinal cord injuries rendering them incontinent. Pyelonephritis, a kidney infection produced by bacterial spread from the lower urinary tract, has been the leading cause of death among paralyzed World War II and Korean war veterans. Neurologic dysfunction of the urinary sphincter can also occur because of multiple sclerosis, stroke, cerebrovascular disease, Parkinson disease and diabetes. Approximately 20% of the population over 65 suffer from incontinence. Women suffer "stress incontinence" largely the result of changes in bladder geometry following child birth. Many men experience incontinence after prostate surgery. Finally, incontinence can result from meningomyelocoele, amyotrophic lateral sclerosis, spinal cord or brain tumor, head injury, herniated disc, syringomyelia and tabes dorsalis.

Various attempts have been made to artificially produce urinary continence. Early attempts to prevent male incontinence involved externally clamping the penis; but, pressure sufficient to stop urinary flow tends also to compromise circulation, causing pain, skin alteration and thrombosis. An analogous application for women, compressing the urethra between the vaginal wall and the pubic bone, shares these disadvantages.

Several implantable artificial sphincters have, more recently, been disclosed in the prior art. U.S. Pat. No. 4,256,093 issued to Curtis Helms et al teaches the use of a fluid filled urethra collar which is contracted by manually squeezing a bulb implanted in the scrotum. In an article entitled "Implantation of an Artificial Sphincter for Urinary Incontinence" by F. B. Scott et al, in *Contemporary Surgery*, Vol. 18, Feb. 1981, results with such prior art artificial sphincters are reported. The article focuses on typical prior art devices which require a bulbous pump to be implanted in the scrotum of the male or in the labium of the female. In order to initiate urine flow the patient must compress the bulbous pump. The prior art devices are psychologically and cosmetically undesirable because of a general aversion most patients have to touching implants in such sensitive portions of the bodies as the scrotum and labium.

U.S. Pat. No. 3,815,576 issued to Donald R. Balaban teaches the use of a fluid filled flexible container implanted in the patient which is squeezed manually to actuate a piston-cylinder in a U-shaped clamp. Similarly, U.S. Pat. No. 4,056,095 issued to Pierre Rey et al and U.S. Pat. No. 4,0178,915 issued to Gerhard Szinicz et al teach the use of a fluid filled artificial sphincter which is actuated by pressing on the subcutaneously implanted membrane. These references share the disadvantage of having no control over the pressure exerted by the artificial sphincter on the urethra once the apparatus is implanted.

During the course of a research study (G. Timm et al, "Experimental Evaluation of an Implantable Externally Controllable Urinary Sphincter", *Investigative Urology* 11:326–330, 1974) it was found that artificial sphincter cuff pressure of 40 cm of $H_2O$ and above produce necrosis (tissue death) of the urethra. As a result, the prior art devices generally operate at a cuff pressure below 40 cm of $H_2O$. However, the normal bladder (and also the hypertrophic bladder), can produce high pressure transients, which results in dripping incontinence for patients with these devices. U.S. Pat. No. 3,744,063 issued to McWhorter et al teaches controlling the flow of a fluid into the sphincter so that pressure applied to the urethra is graduated and controlled. However, variable pressure is controlled manually by applying digital pressure to an implanted pump chamber. Presumably, the patient increases the sphincter pressure after dripping incontinence has occurred and been detected. The patient would not be able to respond to rapid changes in bladder pressure caused by bladder spasms, voluntarily or involuntary tensing of the diaphragm or abdominal wall, or increased intra-abdominal pressure due to walking, sitting, coughing or laughing.

The August 1981 issue of *Urology Times* contains an article reporting on an address by Dr. T. R. Malloy of the Pennsylvania Hospital in Philadelphia. Dr. Malloy has discovered that to reduce necrosis of the urethra it is necessary to have the artificial sphincter unfilled upon initial implant. It was found that urethra tissue swells immediately after surgery. If the artificial sphincter is filled it will exert an excessive pressure on the swollen urethra resulting in tissue necrosis. Dr. Malloy recommends allowing the swelling to decrease, followed by a second operation at a later time, merely to fill the sphincter chamber with fluid. The prior art artificial sphincters have no way of adding or replacing fluid in the artificial sphincter without surgery. Therefore, successful implantation of prior art devices requires two separate surgical operations.

SUMMARY OF THE INVENTION

The present inventor recognized the above-mentioned problems and has invented a manually actuated hydraulic sphincter which automatically increases sphincter pressure with increasing bladder pressure. An implanted hydraulic control unit automatically adjusts sphincter fluid pressure so that the fluid filled artificial sphincter exerts just enough pressure on the urethra to prevent incontinence.

In addition, the present invention has the advantage that the artificial sphincter can be implanted and remain void of fluid until the urethra has healed and swelling been reduced. The invention allows fluid to be added, after implantation, by inserting a hypodermic syringe through an appropriate septum into the invented device and adding fluid until an appropriate sphincter pressure is obtained. The present invention can, therefore, be safely implanted without the need for the repeat operation required in the prior art. Furthermore, in the invented device, pressure exerted by the artificial sphincter can be measured and controlled at any time after implantation. For example, a low sphincter pressure can be initially set (e.g., 10 cm of $H_2O$ above bladder pressure) which minimizes the possibility of urethral necrosis. If this pressure is shown to be insufficient to maintain continence, it can be increased using a simple hypodermic syringe that adds artificial sphincter fluid without requiring surgical intervention. If the minimum pressure required to maintain continence changes with time in a particular patient, it can be modified by adding fluid (to increase sphincter pressure) or removing fluid (to decrease sphincter pressure) by means of a hypodermic syringe. Any similar adjustment to prior art devices would have required an additional surgical operation.

The invented hydraulic control unit automatically maintains sphincter pressure at a set differential above bladder pressure and/or abdominal pressure. This pressure differential is set at the minimal level necessary to provide continence, thereby assuring little or no urethral tissue damage. The cystometrogram of a normal bladder shows a modest rise in pressure with the first 50 cc of fluid followed by a plateau as the fluid volume increased in the range of 100 to 400 cc. When the bladder is filled to greater than 400 cc, the bladder pressure increases rapidly. As bladder pressure increases as indicated above, the pressure exerted by the artificial sphincter of the present invention will correspondingly increase while at the same time retaining a fixed differential value above that bladder pressure.

Bladder pressure or abdominal pressure also can increase rapidly because of bladder spasm, voluntary or involuntary tensing of the diaphragm or abdominal wall, or increased intra-abdominal pressure due to walking, sitting, coughing or laughing. If for example, the patient's bladder or diaphragm spasms, bladder pressure will increase rapidly. To prevent dribbling or stress incontinence the pressure exerted by the artificial sphincter on the urethra may be required to exceed diastolic pressure at least for that short period of time when the bladder pressure exceeds diastolic pressure. Prior art devices, to prevent such dribbling incontinence, would have to constantly maintain sphincter pressure above diastolic pressure thereby causing necrosis of urethral tissue which is permanently damaging. By contrast, the invented apparatus will automatically increase sphincter fluid pressure only for the length of the spasm, thereby causing no threat of tissue necrosis. The invented apparatus therefore can provide continence during bladder pressure peaks without causing necrosis of the urethral tissue. The pressure sensing bulb can be implanted in the wall of the bladder, thereby directly sensing bladder pressure, or it can be placed in the abdomen just below the bladder. When at the latter location, the pressure sensed would be that of abdominal pressure plus to some extent a pressure that is dependent on the extent to which the bladder is filled. Placement in the abdominal area may be advantageous if bladder wall surgery is difficult or contraindicated for a particular patient.

To provide the above-stated advantages, the present invention includes a subcutaneously implanted control unit which is hydraulically connected to: an artificial sphincter which surrounds a portion of the urethra; and, a bladder pressure sensing bulb. The control unit contains the following three fluid filled chambers: an actuation chamber, a sphincter fluid chamber, and a pressure reference chamber. The sphincter fluid chamber is hydraulically coupled to the artificial urethral sphincter such that pressure exerted by the sphincter varies according to the fluid pressure in the sphincter fluid chamber. The pressure reference chamber is hydraulically coupled to the bladder pressure bulb and fluid pressure in the chamber increases as the bladder pressure bulb is compressed by increased bladder or intra-abdominal pressure. A common wall membrane between the sphincter fluid chamber and the pressure reference chamber acts as a pressure differential means automatically maintaining the sphincter fluid at a set pressure differential above the sensed bladder pressure.

An actuation means included in the control unit contains an actuation chamber, an actuation diaphragm and at least one actuation bellows. The actuation diaphragm is positioned on the outer face of the control unit so that it can be pressed by manually applying pressure to the abdominal skin layer immediately above the implant. When the actuation diaphragm is pressed, displaced fluid elongates the actuation bellows. The elongated actuation bellows press against the sphincter fluid chamber's common wall membrane, thereby increasing sphincter fluid chamber volume and lowering the sphincter fluid pressure. In operation, manual pressure applied to the actuation diaphragm reduces sphincter pressure, allowing the patient to freely urinate.

The Manually Actuated Hydraulic Sphincter (MAHS) also contains an invented means for adjusting the fluid pressure level in the hydraulic control unit after implantation. To provide this feature the apparatus includes three septums—an outer septum comprising part of the actuation diaphragm; and, two inner septums each comprising part of the wall separating the two inner chambers. In operation, a non-coring hypodermic needle is inserted through the septums into the desired chamber. A side hole in the hypodermic needle allows the physician access to the fluid so he can measure its pressure or add or remove fluid as desired. This feature allows the physician to replace any lost fluid or to reset the system's parameters, allowing the physician to: (1) adjust the sensitivity of the actuation means to external pressure, (2) adjust the differential pressure exerted by the artificial sphincter; or, (3) adjust the pressure level in the pressure reference chamber so it is reasonably close to actual bladder pressure.

A first novel feature of the invention is a manually actuated hydraulic sphincter which can prevent incontinence, over a wide range of bladder and intra-abdominal pressure, without causing necrosis of the urethral tissue.

A second novel feature of the invention is the use of a control unit which automatically increases sphincter pressure in relation to increases in bladder pressure and/or abdominal pressure.

A third novel feature of the invention is the use of a control unit which has a bladder pressure sensing bulb, implanted in association with the bladder, to sense bladder pressure and/or abdominal pressure.

A fourth novel feature is the use of a control unit which contains a means for adjusting the fluid pressure levels after the unit is implanted.

A fifth novel feature is the use of a manual actuation means which can be adjusted for sensitivity to external pressure, after it is implanted.

A sixth novel feature is the use of a manually actuated hydraulic sphincter which can be adjusted after implantation to set or reset the sphincter pressure.

A seventh novel feature is the use of a manually actuated hydraulic sphincter which can be adjusted to meet the patient's physiological parameters at any time after implantation.

An eighth novel feature is the ability to measure actuation, sensor and reference pressure levels after implantation.

A ninth novel feature is that the bladder pressure sensing bulb is expanded each time MAHS is actuated for voiding thus preventing the build-up of body tissue encapsulation around the sensing bulb.

BRIEF DESCRIPTION OF THE DRAWINGS

FIG. 5 is a diagrammatic view illustrating implantation of the bladder pressure sensing bulb within the detrusor muscle of the bladder wall.

FIG. 6 illustrates the artificial sphincter under three conditions.

FIG. 8 is a cross-sectional view of the hydraulic control unit.

FIG. 9 is a cross-sectional view of the hydraulic control unit which also contains a means for adjusting and measuring fluid pressure level in the control unit after implantation.

FIG. 10 is a perspective view illustrating the insertion of hypodermic needles into the control unit for withdrawing or adding fluid to the various control unit chambers after implantation of the MAHS system and/or from measurement of the fluid pressure in one or more chambers.

DETAILED DESCRIPTION OF THE PREFERRED EMBODIMENT

Figure 1:
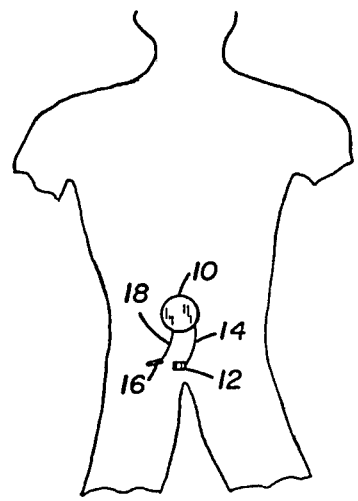
FIG. 1 illustrates the positioning of the various portions of the invented manually actuated hydraulic sphincter within a human body.

The invented apparatus for manually actuating an artificial hydraulic sphincter is illustrated in FIG. 1. The apparatus is generally composed of: an implantable hydraulic control unit 10; an artificial sphincter 12 which is hydraulically coupled by pressure line 14 to the control unit 10; and, a bladder pressure sensing bulb 16 implanted in association with the bladder which is hydraulically coupled by pressure line 18 to control unit 10. In the preferred embodiment of the invention, the control unit is contained in a disk shape casing which is implanted subcutaneously, just beneath the skin, in the patient's abdomen.

Figure 2:
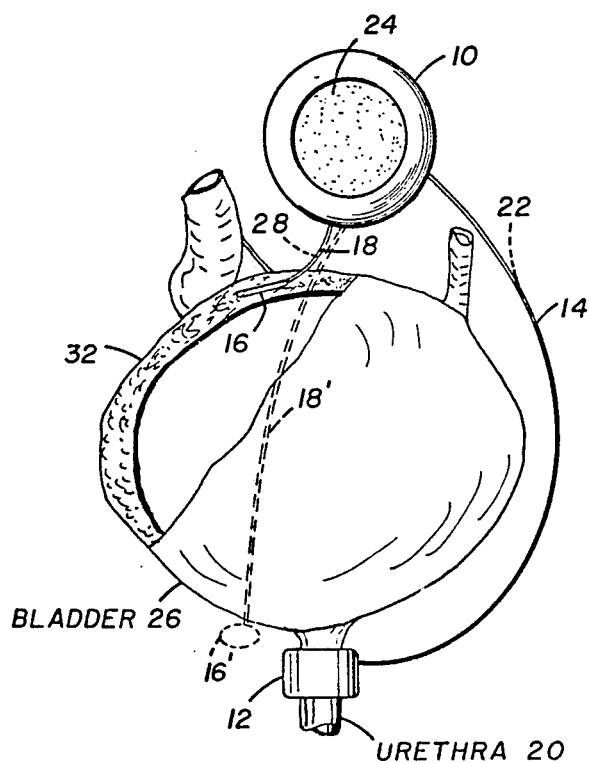
FIG. 2 is a diagrammatic view illustrating the orientation of various portions of the manually actuated hydraulic sphincter relative to the bladder and urethra.

FIG. 2 shows a more detailed view of the invented apparatus. The artificial sphincter 12 is shown surrounding a portion of the urethra 20. The artificial sphincter 12 and associated pressure line 14 are filled with an incompressible sphincter fluid 22. As the sphincter fluid pressure 22 is increased or decreased by control unit 10, the pressure exerted by the artificial sphincter 12 on the urethra will correspondingly increase or decrease. An actuation diaphragm 24 is mounted on the surface of control unit 10 that is just under the skin. When the control unit 10 is implanted subcutaneously, the actuation diaphragm 24 can be pressed by manually applying pressure to the skin just above the implant. As the patient presses and holds down the actuation diaphragm 24, sphincter fluid pressure is reduced, enabling the patient to urinate. As soon as hand pressure is removed, the patient immediately becomes continent. A bladder pressure sensing bulb 16 is implanted in the wall 32 of the bladder 26 and senses bladder fluid pressure by compressing slightly as bladder pressure increases. Alternatively, the bladder pressure sensing bulb 16' can be placed anywhere in the abdomen specifically in the abdomen just below the bladder. When at this location the bulb can sense abdominal pressure plus to some extent a pressure which is dependent on bladder volume. The bladder pressure sensing bulb 16 (alternatively, bladder pressure sensing bulb 16') is filled with an incompressible reference pressure fluid 28, and is hydraulically linked by line 18 (alternatively, line 18') to control unit 10. Control unit 10 in turn is adjusted so that the sphincter fluid pressure is set at a minimum pressure differential necessary to avoid tissue damage while maintaining continence.

Figure 3:
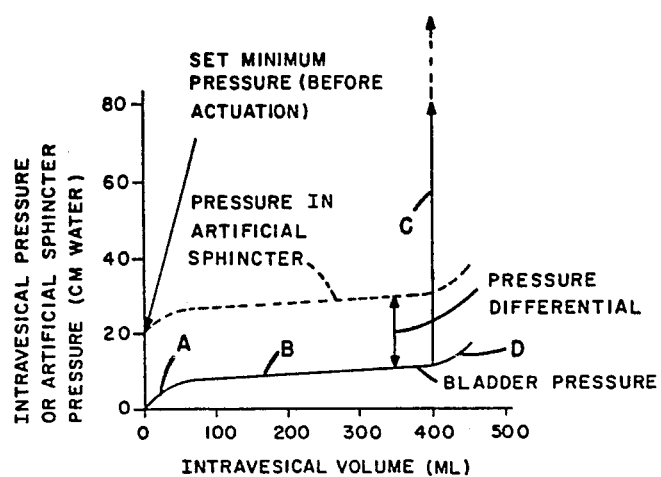
FIG. 3 is a cystometrogram, graphically showing bladder pressure as a function of urinary volume and the corresponding pressure in the artificial sphincter.

The contractile responses of the bladder in the presence of increased urinary volume are displayed in the cystometrogram, illustrated in FIG. 3. The cystometrogram of a normal bladder shows a modest rise in pressure with the first 50 cc of fluid (segment A) followed by a plateau as the fluid volume increases from 100 to 400 cc (segment B). When the normal bladder is filled to greater than 400 cc the bladder pressure increases rapidly (segment D). Occasionally there will be a bladder spasm which causes a pressure spike as shown by segment C of FIG. 3. The invented hydraulic control unit (MAHS) automatically tends to maintain sphincter pressure at a differential value above bladder pressure as is shown by the dotted line in FIG. 3. As bladder pressure increases, along segment A, B, C or D of the cystometrogram, the pressure exerted by the artificial sphincter will be correspondingly increased, by control unit 10, by some fixed differential valve, such as 20 cm of $H_2O$ as illustrated in FIG. 3.

Figure 4:
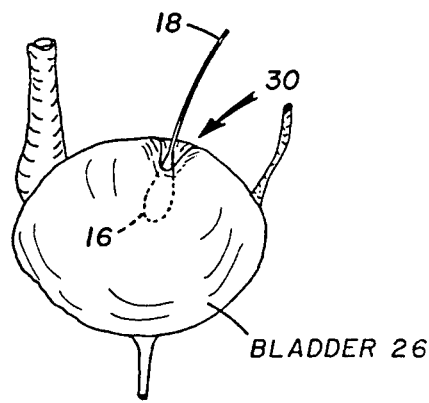
FIG. 4 is a diagrammatic view of the bladder pressure bulb implanted within the bladder wall.

FIGS. 4 and 5 illustrate two possible methods of surgically attaching the pressure sensing bulb 16 to the bladder 26. FIG. 4 shows the bladder pressure sensing bulb 16 plicated into the wall of the bladder 26. Surgical sutures at the opening of the plication 30 hold the bladder pressure bulb in place. FIG. 5 shows an alternative placement of the bladder pressure bulb near the interior of the detrusor muscle 32. The detrusor muscle 32 is dissected by known medical techniques and a flat bladder pressure bulb is placed therein. In operation, as the bladder fluid pressure increases the surgically implanted bladder pressure sensing sensing bulb 16 will be compressed and fluid pressure in the bulb will increase. The bladder pressure sensing bulb 16 can be made from medical grade silicon rubber or bromo-butyl rubber and is of a wall like construction. The bulb 16 can have a limited fluid volume so that if bladder pressure exceeds a predetermined limit all the fluid is driven out of the bulb 16 and the sphincter pressure will then not continue to increase with increasing bladder pressure. Thus, if the patient becomes unconscious and bladder pressure exceeds, let us say, 100 cm of the H₂O, then urine will start to flow out through the urethra.

Figure 6A:
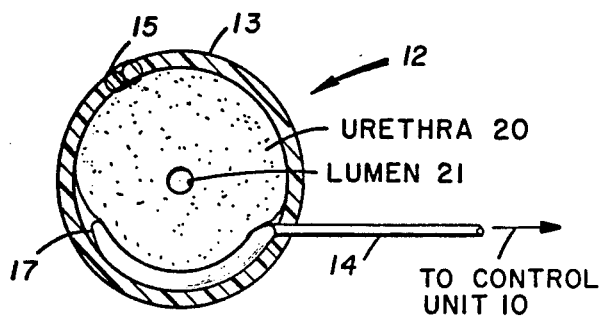
FIG. 6A shows a swollen urethra after surgery and an unfilled sphincter bulb to avoid tissue damage.

FIG. 6 shows three views of the artificial urethral sphincter, 12. FIG. 6A shows the urethra 20, in a swollen condition which occurs soon after surgery and lasts for several days. A circumferential sheath 13, approximately 2 cm long and made from an implantable cloth material such as Dacron, is wrapped around the urethra and sewn together along a seam (as shown in FIG. 6) by surgical thread 15. Although the urethra 20, is swollen, the lumen 21, through which the urine must pass, remains open because the sphincter bulb 17, is unfilled at this time.

Figure 6B:
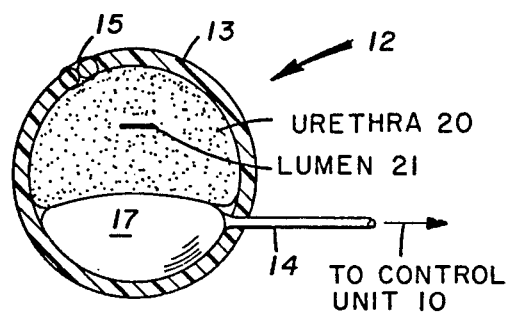
FIG. 6B shows a urethra which is no longer swollen and shows the lumen closed by a filled sphincter bulb.
Figure 6C:
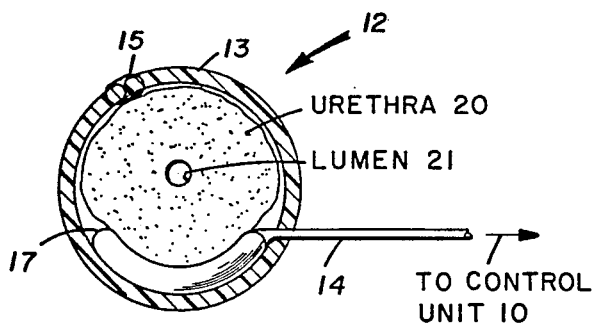
FIG. 6C shows the lumen opened for voiding after fluid is removed from the sphincter bulb.

When urethral swelling has decreased to an acceptable level, the bulb 17, can be filled with sphincter fluid as shown in FIG. 6B causing the urethra 20, to be compressed and the lumen 21, to be closed thus providing continence. FIG. 6C shows the bulb 17, with fluid decreased to the point so that the lumen 21, is opened and the patient can then void. Control of the fluid level in the bulb 17, is accomplished by means of the control unit 10, which is shown in FIGS. 1, 2, 8 and 9.

Figure 7A:
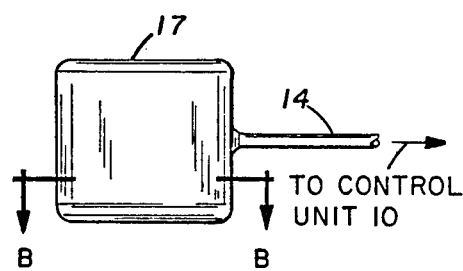
FIG. 7A illustrates construction details of the sphincter bulb.
Figure 7B:
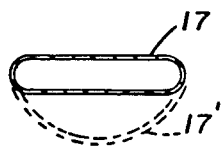
FIG. 7B illustrates cross-sections of the sphincter bulb when filled to provide continence and when emptied to allow urination.

FIG. 7 shows some construction details of the sphincter bulb 17. FIG. 7A is a plan view of the sphincter bulb 17, which is connected by line 14 to the control unit 10 (not shown in FIG. 7). The sphincter bulb 17 might be approximately 2 cm long and 1 cm across and would be fabricated from medical grade silicon rubber or bromobutyl rubber. FIG. 7B shows a cross-section of the bulb 17 at low fluid level (for voiding), and the expanded bulb 17' illustrates a cross-section at a fluid level high enough to maintain continence.

FIG. 8 is a cross-section of the manually actuated hydraulic control unit 10. Actuation chamber 34 is mounted inside the outer casing 36 of control unit 10. The upper wall of the actuation chamber 34 contains a flexible actuation diaphragm 24 which is positioned on the front surface of the outer casing 36 that is just beneath the patient's skin. The diaphragm 24 might be fabricated from titanium metal and might be 1 to 10 mils thick and have a corrugated pattern as shown in FIG. 8. The diaphragm 24 might otherwise be fabricated from an elastomer such as medical grade silicone or bromobutyl rubber. The actuation chamber's lower wall 38 contains at least one flexible actuation bellows 40. In the preferred embodiment, four actuation bellows are equally spaced along the inner circumference of the actuation chamber's lower wall and are connected at their lower extremity to torroidal actuation ring 41 (only two of the actuation bellows are shown in the cross-sectional view of FIG. 8). The bellows might be fabricated from thin metal or an elastomer. The actuation chamber 34 is filled with an incompressible actuation fluid 42. The actuation chamber 34, flexible actuation diaphragm 24 and actuation bellows 40, act as a means for actuating the artificial sphincter. Pressing on the flexible actuation diaphragm 24, causes the incompressible actuation fluid 42 to be displaced and to elongate the actuation bellows 40.

Sphincter fluid chamber 44 is mounted inside outer casing 36 adjacent to the actuation chamber 34 and is hydraulically connected by pressure line 14 to the artificial urethral sphincter 12. In the preferred embodiment, the actuation chamber's lower wall 38 also forms the upper wall of the sphincter fluid chamber 44. The sphincter fluid chamber's lower wall 46 contains an elastic diaphragm, that is positioned such that as actuation bellows 40 become elongated they press against the elastic diaphragm 46. The sphincter fluid chamber 44, is filled with an incompressible sphincter fluid 22. The spring force exerted by elastic diaphragm 46 tends to keep the sphincter fluid 22 in the chamber 44, in the pressure line 14 and in the sphincter bulb 17 at a predetermined minimum differential pressure above that pressure of the pressure reference chamber 48. In addition, when the actuation bellows 40 are elongated they press against the elastic diaphragm 46 increasing the volume of the sphincter fluid chamber 44 and decreasing the pressure of the sphincter fluid 22, thereby allowing the urethral sphincter 12 to decrease in volume and pressure and therefore the patient can urinate. A spacing 47 separates the bottom of torroidal actuation ring 41 from elastic diaphragm 46, preventing inadvertent urination due to spurious pressure on the actuation diaphragm 24.

Pressure reference chamber 48 is located in the lower section of rigid outer casing 36 and is hydraulically connected by pressure line 18 to bladder pressure sensing bulb 16 (not shown in FIG. 8). Pressure reference chamber 48 is located below the sphincter fluid chamber 44, such that elastic diaphragm 46 is a common wall separating the pressure reference chamber 48 and sphincter fluid chamber 44. The pressure reference chamber 48, pressure line 18 and bladder pressure sensing bulb 16 are all filled with an incompressible reference pressure fluid 28. An increase in fluid pressure in the pressure reference chamber 48, will result when the bladder pressure sensing bulb 16 (not shown in FIG. 8) is tending toward compression by increased abdominal pressure and increased bladder volume or pressure. An increase in fluid pressure in the reference pressure chamber 48 will cause elastic diaphragm 46 to flex thereby decreasing the volume of the sphincter fluid chamber 44 and increasing the sphincter fluid pressure. This interaction between the pressure reference chamber 48 and the sphincter fluid chamber 44 provides a means for obtaining continence while providing minimal applied pressure to the urethra for all conditions of the bladder. This pressure differential means maintains a set (and nearly constant) pressure differential between the pressure exerted by the artificial sphincter 12 and pressure sensed by the bladder pressure sensing bulb 16. The spring force of elastic diaphragm 46, is a means to maintain a minimal differential sphincter fluid pressure so as to provide continence without urethral necrosis. As the bladder pressure increases or as abdominal pressure increases, bladder pressure sensing bulb 16 will tend to compress causing an increase in reference fluid pressure which causes elastic diaphragm 46 to flex, and correspondingly increases sphincter fluid pressure above the set minimal value. This pressure differential means assures that sphincter fluid pressure is greater than the sensed bladder pressure or sensed abdominal pressure. Pressure exerted by the artificial sphincter on the urethra will track with bladder pressure and/or abdominal pressure. In the preferred embodiment, the differential sphincter fluid pressure might be 20 to 60 cms. of water. The absolute value of the sphincter fluid pressure will increase as the bladder fills or as abdominal pressure increases.

In fact, the elasticity of several of the MAHS components will cause some deviation from an exactly constant differential pressure. But this will not cause the desired result, namely, a urethral sphincter pressure to be always above the bladder pressure and/or abdominal pressure to be significantly compromised.

In operation, the invented apparatus automatically adjusts sphincter fluid pressure so that the artificial sphincter exerts the minimum pressure necessary to maintain continence without causing urethral necrosis. Sphincter fluid pressure is automatically adjusted to compensate for increases in bladder pressure due to bladder fill, bladder spasm, voluntarily or involuntary tensing of the diaphragm or abdominal wall, or increased intra-abdominal pressure due to walking, sitting, coughing or laughing. To urinate, the patient places his fingers on the skin over the center of the implanted apparatus and presses vigorously with his fingers on the actuation diaphragm 24. This action causes the elongation of actuation bellows 40 which in turn enlarge the sphincter fluid chamber, reducing sphincter fluid pressure. It will be noted in FIG. 8 that a small distance is maintained between the non-extended actuation bellows 40 and the elastic diaphragm 46. The small distance assures that a slight increase in pressure on the actuation diaphragm will not result in inadvertent urination.

Another feature of MAHS is that, when voiding takes place, the pressure in the pressure sensing bulb 16 is increased thus increasing its volume. This size change is intended to prevent encapsulation of the bulb 16 by the growth of body tissue around the bulb 16. Thus, the bulb 16 will remain functional, i.e., continue to accurately sense pressure.

FIGS. 9 and 10 show an invented means for measuring and adjusting fluid pressure in the control unit 10 while it is implanted. An outer septum 50 is mounted in a rigid ring 52 which is itself mounted in the center portion of the actuation diaphragm 24. Outer septum 50 is made from self-sealing material so that a non-coring type hypodermic needle can penetrate the septum and be withdrawn without causing the seal to leak. The septum could, for example, be made from medical grade silicon or bromo-butyl rubber. Two inner septums 54, 56 are mounted on a rigid center support ring 58. The first inner septum 54 becomes part of the rigid wall 38 separating the actuation chamber 34 from the sphincter fluid chamber 44. The second inner septum 56 provides a section of the wall separating the sphincter fluid chamber 44 and the pressure reference chamber 48. Elastic membrane 46, is attached between the rigid center support ring 58 and the outer casing 36 and provides the remainder of the common wall separating these two chambers. The center support ring 58, contains fluid passageways 60 and 61 which allow respectively sphincter fluid and pressure reference fluid to freely flow within their respective chambers.

FIG. 10, is an enlarged cross-section view showing three hypodermic needles passing through each of the three septums. The hypodermic needles are used in conjunction with the septums as a means to: (1) replenish any of the three fluids, (2) adjust the pressure and fluid volume in each of the three fluid chambers, and (3) provide a means for measurement of the pressure in each of the three fluid chambers. Hypodermic needles 62, 64, 66 are of the non-coring type with side holds for adding or withdrawing fluid and making pressure measurements. The position of the side hole relative to the end of the hypodermic needle determines which of the three fluid chambers can be accessed by that specific hypodermic needle. Any one of the three hypodermic needles could be connected by tubing to a pressure gauge 68 and a syringe 70 thereby allowing fluid pressure in a specific chamber to be measured. This allows the physician to adjust fluid pressure by adding or removing fluid.

In operation, if a patient does not remain continent at a sphincter fluid pressure of, for example, 40 cms. of water, the center hypodermic 64 can be inserted through all three septums with its side hole entering the sphincter fluid chamber 44. When center hypodermic 64 is positioned as shown in FIG. 8, the pressure gauge will read the sphincter fluid pressure and the physician would then know the pressure exerted by the artificial sphincter on the urethra. If a change in sphincter fluid pressure is desired, fluid can be added to or removed from sphincter fluid chamber 44. When fluid is added, the pressure exerted by the artificial sphincter will be increased; when fluid is removed the pressure exerted by the artificial sphincter is decreased.

Hypodermic needle 62 shown in FIG. 10, is designed to measure the fluid pressure in pressure reference chamber 48. To assure that the fluid in the pressure reference chamber 48 is at a pressure reasonably close to bladder pressure, the urologist can measure bladder pressure directly using a urethral catheter and compare that value with the pressure measured in pressure reference chamber 48. As mentioned previously, fluid can be added or removed as necessary to adjust pressure in the reference chamber to be closely equal to bladder pressure and/or abdominal pressure.

Similarly, hypodermic needle 66 shown in FIG. 10, is designed to access fluid in actuation chamber 34. If the patient is inadvertently urinating because of spurious pressure on actuation diaphragm 24, actuation fluid could be removed, thereby, increasing the separation 47 of the actuation bellows 40 from the elastic diaphragm 46, which would tend to decrease the possibility of inadvertent urination.

Although it is probable that only one hypodermic may be used at any one time, the use of two or three of such needles might be utilized to determine the interactions of the various fluids within the hydraulic control unit. Furthermore, one or more needles might be used in conjunction with a urinary catheter connected to a pressure gauge that measures bladder pressure directly. Also, the invented means for measuring and varying fluid pressure in the hydraulic control unit could have application in a simplified two-chamber hydraulic control unit. The two chamber design would have an actuation chamber and a sphincter fluid chamber and could be used to control an artificial urinary sphincter when sensing bladder pressure is not desired. The two chamber design could be used in an artificial anal sphincter.

In the preferred embodiment, all metal parts used in the hydraulic control unit 10, could be fabricated from pure titanium and the outer titanium casing 36, would have an upper half 36' and a lower half 36" allowing for simpler fabrication. The septums, as has been mentioned previously, could be made from medical grade silicon or bromo-butyl rubber. All three fluids could be normal saline (5% NaCl in $H_2O$) or silicon fluid or any other fluid that would not cause harm to the patient if inadvertently released.

Obviously many modifications and variations of the present invention are possible in light of the above teaching. It is therefore to be understood that within the scope of the appended claims the invention may be practiced otherwise than as specifically described.

What is claimed and desired to be secured by Letters Patent of the United States is:

1. An implantable hydraulic urinary sphincter system comprising:
   a control unit contained in a casing and implanted in a subcutaneous position, comprising:
   an actuation chamber filled with an incompressible actuation fluid, said actuation chamber mounted inside said casing, a first wall of said actuation chamber containing a flexible actuation diaphragm positioned on said casing, at least part of said first wall of said actuation chamber containing an outer septum, a second wall of said actuation chamber containing at least one extensible portion, pressing on said flexible actuation diaphragm causes said at least one extensible portion to elongate, at least part of said second wall including an inner septum, said inner septum located below said outer septum;
   a sphincter fluid chamber filled with an incompressible sphincter fluid, said sphincter fluid chamber mounted inside said casing, the second wall of said actuation chamber also forming at least part of one wall of said sphincter fluid chamber, an additional wall of said sphincter fluid chamber containing an elastic diaphragm, said elastic diaphragm maintaining said sphincter fluid at a minimum pressure, said sphincter fluid chamber positioned adjacent to said actuation chamber such that said at least one extensible portion when elongated presses against said elastic diaphragm increasing the volume of said sphincter fluid chamber and decreasing the pressure on said sphincter fluid thereby allowing said patient to urinate; and,
   an artificial sphincter directly coupled hydraulically to said sphincter fluid chamber, said artificial sphincter chamber being pressurized at a fluid pressure essentially equal to said sphincter fluid; and,
   an access means for selectively accessing fluid in said actuation fluid chamber and said sphincter fluid chamber after said control unit has been implanted.

2. The apparatus of claim 1, wherein said access means comprises:
   a needle for simultaneously penetrating said outer, and said inner septums and for accessing fluid in said control unit.

3. The apparatus of claim 2, wherein said needle means is a non-coring hypodermic needle having a side hole.

4. The apparatus of claim 2, wherein said side hole is positioned a first distance from the tip of said needle means, said first distance allowing said needle means selective access to fluid in said actuation chamber when said tip of said needle means is positioned abutting the bottom of said inside casing.

5. The apparatus of claim 2, wherein said side hole is positioned a second distance from the tip of said needle means, said second distance allowing said needle means selective access to fluid in said sphincter fluid chamber when said tip of said needle means is positioned abutting the bottom of said inside casing thereby allowing physician to set said minimum sphincter pressure.

6. The apparatus of claim 1, wherein said outer, and said inner septums are made from a self-sealing material.

7. The apparatus of claim 4, futher including a pressure gauge connected to said needle means for measuring fluid pressure.

8. The apparatus of claim 4 further including a syringe connected to said needle means for removing fluid.

9. The apparatus of claim 2, wherein said needle means includes a first and a second non-coring hypodermic needle, each having a side hole, each of said two hypodermic needles connected to a pressure gauge, and the side hole of said first hypodermic needle is adapted to be inserted in fluid communication with said actuation chamber and said second hypodermic needle in fluid connected with said sphincter fluid chamber, so that fluid pressure in each fluid chamber chamber can be simultaneously monitored.

10. The apparatus of claim 2, wherein said needle means includes a first and a second non-coring hypodermic needles each having a side hole, each of said at least two hypodermic needles connected to a syringe and the side hole of said first hypodermic needle is adapted to be inserted in fluid connected said actuation chamber and said second hypodermic needle in fluid communication with said sphincter fluid chamber, so that the fluid volume in each chamber can be simultaneously adjusted.

11. An implantable hydraulic urinary sphincter system comprising:
    a control unit contained in a casing and implanted in a subcutaneous position, comprising:
    a first chamber filled with an incompressible fluid, said first chamber mounted inside said causing,
    a second chamber filled with an incompressible fluid, said second chamber mounted inside said casing and below said first chamber, one wall of said first chamber also forming at least part of a wall of said second chamber,
    an outer septum mounted on said casing and forming part of said first chamber,
    an inner septum forming part of said wall formed between said first and second chambers and located below said outer septum; and,
    a needle means including at least two non-coring hypodermic needles, each having a side hole, each of said at least two hypodermic needles connected to a pressure gauge, and each of said at least two hypodermic needles is adapted to be inserted in fluid communication with a different fluid chamber, so that fluid pressure in each fluid chamber can be simultaneously monitored.

12. An implantable hydraulic urinary sphincter system comprising:
    a control unit contained in a casing and implanted in a subcutaneous position, comprising:
    a first chamber filled with an incompressible fluid, said first chamber mounted inside said casing,
    a second chamber filled with an incompressible fluid, said second chamber mounted inside said casing, and below said first chamber, one wall of said first chamber also forming at least part of a wall of said second chamber,
    an outer septum mounted on said casing and forming part of said first chamber,
    an inner septum forming part of said wall formed between said first and second chambers and located below said outer septum; and,
    a needle means including at least two non-coring hypodermic needles, each having a side hole, each of said at least two hypodermic needles connected to a syringe, and each of said at least two hypodermic needles is adapted to be inserted in fluid communication with a different fluid chamber, so that the fluid volume in each chamber can be simultaneously adjusted.

* * * * *